US012625125B2

(12) United States Patent
Ishida et al.

(10) Patent No.: US 12,625,125 B2
(45) Date of Patent: May 12, 2026

(54) METHOD OF EVALUATING CENTRAL SEGREGATION IN STEEL

(71) Applicant: JFE STEEL CORPORATION, Tokyo (JP)

(72) Inventors: Tomoharu Ishida, Tokyo (JP); Seiya Sugawara, Tokyo (JP); Kenji Tsuzumi, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 300 days.

(21) Appl. No.: 18/256,096

(22) PCT Filed: Sep. 6, 2021

(86) PCT No.: PCT/JP2021/032733
§ 371 (c)(1),
(2) Date: Jun. 6, 2023

(87) PCT Pub. No.: WO2022/130703
PCT Pub. Date: Jun. 23, 2022

(65) Prior Publication Data
US 2024/0044822 A1      Feb. 8, 2024

(30) Foreign Application Priority Data
Dec. 18, 2020      (JP) ................................. 2020-210746

(51) Int. Cl.
*G01N 33/2028* (2019.01)
*G01N 23/2251* (2018.01)
(Continued)

(52) U.S. Cl.
CPC ..... *G01N 33/2028* (2019.01); *G01N 23/2251* (2013.01); *G01N 23/2252* (2013.01);
(Continued)

(58) Field of Classification Search
CPC .......... G01N 23/2251; G01N 23/2252; G01N 33/20; G01N 33/2028; G01N 2223/402; G01N 2223/418; G01N 2223/624
See application file for complete search history.

(56) References Cited

U.S. PATENT DOCUMENTS

2010/0326559 A1      12/2010  Ishikawa et al.
2020/0141023 A1       5/2020  Mizukami

FOREIGN PATENT DOCUMENTS

CN            105445306 A      3/2016
CN            108139306 A      6/2018
(Continued)

OTHER PUBLICATIONS

Mizukami et al. "Development of Analysis Method for Sulfide in Steel with Chelating Agent of Copper"—published Sep. 19, 2019 (Year: 2019).*
(Continued)

*Primary Examiner* — Benjamin R Schmitt
(74) *Attorney, Agent, or Firm* — KENJA IP LAW PC

(57)            ABSTRACT

A method of evaluating central segregation in steel with excellent correlation with HIC susceptibility is provided. A method of evaluating central segregation in steel includes: taking a sample from a steel, the sample having a cross section including a central segregation area; measuring an area ratio of an inclusion containing a segregation metal element in a region to be measured including the central segregation area in the cross section; and evaluating central segregation in the steel based on the area ratio measured.

6 Claims, 2 Drawing Sheets

(51) Int. Cl.
   *G01N 23/2252*    (2018.01)
   *G01N 33/20*    (2019.01)

(52) U.S. Cl.
   CPC ....... *G01N 33/20* (2013.01); *G01N 2223/402* (2013.01); *G01N 2223/418* (2013.01); *G01N 2223/624* (2013.01)

(56) References Cited

FOREIGN PATENT DOCUMENTS

| | | | |
|---|---|---|---|
| CN | 108593649 A | 9/2018 | |
| JP | H0224542 A | 1/1990 | |
| JP | H06271974 A | 9/1994 | |
| JP | H09178733 A | 7/1997 | |
| JP | 2006063351 A | 3/2006 | |
| JP | 2009236842 A | 10/2009 | |
| JP | 2013145221 A | 7/2013 | |
| JP | 2013190319 A | 9/2013 | |
| JP | 2014077642 A * | 5/2014 | ........... G01N 23/225 |
| JP | 2015063478 A | 4/2015 | |
| KR | 1020170075061 A | 7/2017 | |
| WO | 2009061006 A1 | 5/2009 | |

OTHER PUBLICATIONS

Nov. 22, 2021, International Search Report issued in the International Patent Application No. PCT/JP2021/032733.

Shigeki Abe, Solubility Products of Metal Sulfides and Electronegativity, Chemical Education, 1978, pp. 188-190, vol. 26, No. 2, The Chemical Society of Japan.

Toshio Shiraiwa et al., Unusual Structure Related to the Segregation in Continuously Casting and Ingot Making Steels, Tetsu-to-Hagane, 1978, pp. 411-419, vol. 64, No. 3.

Apr. 1, 2025, the Extended European Search Report issued by the European Patent Office in the corresponding European Patent Application No. 21906068.8.

Kazumi Mizukami et al., Development of Analysis Method for Sulfide in Steel with Chelating Agent of Copper, ISIJ International, 2020, pp. 120-127, vol. 60, No. 1.

M.A. Mohtadi-Bonab et al., A comparative study of hydrogen induced cracking behavior in API 5L X60 and X70 pipeline steels, Engineering Failure Analysis, 2013, pp. 163-175, vol. 33.

Guo Hong-Hai et al., Effect of rare earth elements on macrosegregation in weather-resisting steel, Journal of University of Science and Technology Beijing, Jan. 2010, vol. 32, No. 1.

Jul. 9, 2025, Office Action issued by the China National Intellectual Property Administration in the corresponding Chinese Patent Application No. 202180084911.5 with English language search report.

Jan. 30, 2026, Office Action issued by the China National Intellectual Property Administration in the corresponding Chinese Patent Application No. 202180084911.5 with English language search report.

* cited by examiner

METHOD OF EVALUATING CENTRAL SEGREGATION IN STEEL

TECHNICAL FIELD

This disclosure relates to a method of evaluating central segregation in steel.

BACKGROUND

Central segregation, which occurs during the steelmaking process, is known to cause quality deterioration in various products. In particular, hydrogen induced cracking (HIC) has become a common problem in line pipes used to transport crude oil, natural gas, and other materials that contain large amounts of hydrogen sulfide, because hydrogen tends to penetrate into the steel from the surface. In a central segregation area in a steel material, there are inclusions such as stretched MnS, oxides, and carbides, which tend to accumulate hydrogen that has penetrated into the steel. Accordingly, in such central segregation area, hydrogen-induced cracking is likely to occur frequently. For this reason, a variety of technological developments have been made to measure and reduce central segregation.

Typical methods of evaluating central segregation include the macro corrosion method, the slice method, and the H-print method, which are widely used. In the macro corrosion, a cut surface of a cast steel or a steel plate including a central segregation area is polished, and then macro-corroded with corrosion liquid such as picric acid to visually observe the occurrence of central segregation on the cut surface. In the slice method, the concentration distribution of the segregation metal is determined in the thickness direction by sequentially analyzing the components of the chips collected by slicing a cast steel or a steel plate in the thickness direction from the surface in a stepwise manner. In the H-print method, a cut surface of a cast steel or a steel plate including a central segregation area is macro corroded, and then measurements are made to determine the maximum grain size, etc. in the central segregation area from the print copied from the cut surface.

However, JP H6-271974 A (PTL 1) describes that even after the macroscopic segregation that is the subject of the central segregation evaluation methods is eliminated, if there are spot segregation areas of Mn, MnS may form in groups in such spot segregation areas, and these groups of MnS may become initiation points of HIC.

Several methods are known to evaluate microscopic central segregation as found in these Mn spot segregation areas. For example, PTL 1 describes a method of using an electron probe micro-analyzer (EPMA) to perform mapping analysis of Mn in a cross-section of a line pipe, including a central segregation area, to measure the size of Mn spot segregation areas with Mn concentrations at least 1.32 times higher than the average Mn concentration. JP H9-178733 A (PTL 2) describes a method of measuring the hardness of the axial center of a continuous cast steel and ascertaining the degree of central segregation of the continuous cast steel based on one or more of the average value, maximum value, and difference between the maximum and minimum values of the measured hardness values. In addition, JP 2009-236842 A (PTL 3) describes a method in which a C-section (a cross-section perpendicular to the casting direction or rolling direction) of a continuously cast steel or a steel plate is polished, mapping analysis of an indicator element (segregation metal element) is performed in the region to be measured including a central segregation area in the C-section using EPMA, etc. to determine the area of a region where the concentration of the indicator element is equal to or greater than a predetermined threshold concentration, and then the central segregation is evaluated based on that area or the area ratio relative to the region to be measured. Another conventional evaluation method is to determine the average concentration of an indicator element in a central segregation area and the base metal as the matrix, and to evaluate central segregation by dividing the average concentration in the central segregation area by the average concentration in the base metal.

CITATION LIST

Patent Literature

PTL 1: JP H6-271974 A
PTL 2: JP H9-178733 A
PTL 3: JP 2009-236842 A

SUMMARY

Technical Problem

In general, the degree of central segregation of a cast steel is not uniform in the C-section in the thickness and widthwise directions. Therefore, in order to investigate the central segregation of a cast steel or a steel plate, it is necessary to evaluate the central segregation over a wide area of the C-section. However, if an attempt is made to evaluate the full width of the cast steel by the method of PTL 2, it is necessary to measure the hardness of all the central segregation areas, which is very time-consuming to measure. Furthermore, when determining the maximum value of hardness, it is necessary to statistically measure hardness at many more positions to ensure that the value obtained at that position is the maximum value, which requires a long time for measurement. Although the methods described in PTLs 1 and 3 and the aforementioned conventional evaluation method have the merit of being able to evaluate the central segregation of a cast steel or a steel plate quantitatively, precisely, and relatively quickly over a wide area, they could not provide a sufficient correlation with the crack area ratio (CAR) in the HIC test, and the correlation between central segregation and the occurrence of HIC is unclear. Therefore, there is a possibility of overestimating or underestimating the effect of the degree of segregation on HIC occurrence. In other words, the methods described in PTLs 1 and 3 and the aforementioned conventional evaluation method have not yet reached the point of evaluating the HIC susceptibility of steel materials, although the concentration distribution of the target segregation metal element can be clarified.

It would thus be helpful to provide a method of evaluating central segregation in steel with excellent correlation with HIC susceptibility.

Solution to Problem

The present inventors believed that the reason why the evaluation methods of PTLs 1 and 3 and the aforementioned conventional evaluation method do not provide sufficient correlation with the crack area ratio (CAR) in the HIC test is because they simply evaluate only the concentration distribution of segregation metal elements such as Mn. That is, for example, even if the same concentration of Mn is present in a certain region, the effect on HIC properties is different when Mn is condensed in Fe and when MnS is formed, and it was considered necessary to distinguish between these two cases. The present inventors then found that the area ratio of an inclusion containing a segregation metal element correlated better with CAR than the area ratio of the segregation metal element, and completed the present disclosure.

Furthermore, the present inventors found a suitable method for determining the area ratio of an inclusion containing a segregation metal element. To determine the area ratio of the inclusion, basically, elemental mapping of the constituent elements of the inclusion, for example, can be performed. In this respect, a central segregation area in steel is formed when solute elements in the steel are condensed on the unconsolidated liquid phase side due to redistribution during the solidification process. In other words, the constituent elements of the inclusion in the central segregation area are also present in the matrix, the base metal, albeit in low concentrations. Therefore, if an inclusion is modified with an element that is not present in the base metal, it can be clearly identified by elemental analysis, and the area ratio of the inclusion can be quantified more conveniently and with higher sensitivity.

Therefore, the present inventors noted from their experience that Ag was often detected in MnS when observing MnS in steel by SEM or other means. This was thought to be because the solubility product of $Ag_2S$ is smaller than that of MnS, and Ag, which exists as an inevitable impurity in steel on the ppm order, leached into the electrolytic solution during electrolytic etching of the sample surface for observation, and the Mn in MnS replaced this Ag. Therefore, we conceived a method to accurately determine the area ratio of an inclusion by treating the analysis surface with a solution in which ions of a metal element N (in the above example, Ag ions) in a compound $N_{x2}A_{y2}$, which has a smaller solubility product than an inclusion $M_{x1}A_{y1}$, are added beforehand, to modify the inclusion with N, and measuring the area ratio of N.

The primary features of the present disclosure, completed based on the above findings, are as follows.

[1] A method of evaluating central segregation in steel, the method comprising:

taking a sample from a steel, the sample having a cross section including a central segregation area;

measuring an area ratio of an inclusion containing a segregation metal element in a region to be measured including the central segregation area in the cross section; and evaluating central segregation in the steel based on the area ratio measured.

[2] The method of evaluating central segregation in steel according to aspect [1], where letting $M_{x1}A_{y1}$ be the inclusion and $N_{x2}A_{y2}$ be a compound with a smaller solubility product than $M_{x1}A_{y1}$, the method further comprising:

treating the region to be measured in the sample with a solution containing ions of an element N to replace M located on a surface of the inclusion exposed in the region to be measured with N;

then, measuring an area ratio of the element N in the region to be measured; and using the area ratio of the element N measured as the area ratio of the inclusion, where M denotes the segregation metal element contained in the inclusion, N denotes a metal element other than M, A denotes an element that combines with the element M to form the inclusion and combines with the element N to form the compound, x1 and y1 each denote a numerical value representing a composition ratio of the inclusion, and x2 and y2 each denote a numerical value representing a composition ratio of the compound.

[3] The method of evaluating central segregation in steel according to aspect [2], wherein M is Mn, A is S, and N is Ag.

[4] The method of evaluating central segregation in steel according to aspect [2] or [3], the method further comprising:

performing mapping analysis of the element N in the region to be measured using EPMA;

determining an area ratio of a region where the element N is detected at or above a predetermined concentration in the region to be measured; and using the area ratio as the area ratio of the element N.

[5] The method of evaluating central segregation in steel according to aspect [2] or [3], the method further comprising:

acquiring an SEM image of the region to be measured;

selecting a candidate region based on contrast in the SEM image, the candidate region being a candidate for the inclusion;

performing SEM-EDS analysis on the candidate region to identify a region where the element N is detected at or above a predetermined concentration;

determining an area ratio of the region in the region to be measured; and using the area ratio the an area ratio of the element N.

[6] The method of evaluating central segregation in steel according to aspect [5], wherein the SEM image is a reflected electron image.

[7] The method of evaluating central segregation in steel according to any one of aspects [1] to [6], wherein the steel is a cast steel, a steel plate, or a steel sheet.

[8] The method of evaluating central segregation in steel according to aspect [7], wherein the cross section is a cross section perpendicular to a casting direction of the cast steel, a cross section perpendicular to a rolling direction of the steel plate, or a cross section perpendicular to a rolling direction of the steel sheet.

Advantageous Effect

The method of evaluating central segregation in steel according to the present disclosure can be used to evaluate central segregation with excellent correlation with HIC susceptibility.

DETAILED DESCRIPTION

Figure 1:
FIG. 1 is a graph of the relationship between the area ratio of Ag and the CAR in the mid-thickness part in our examples.
Figure 1:
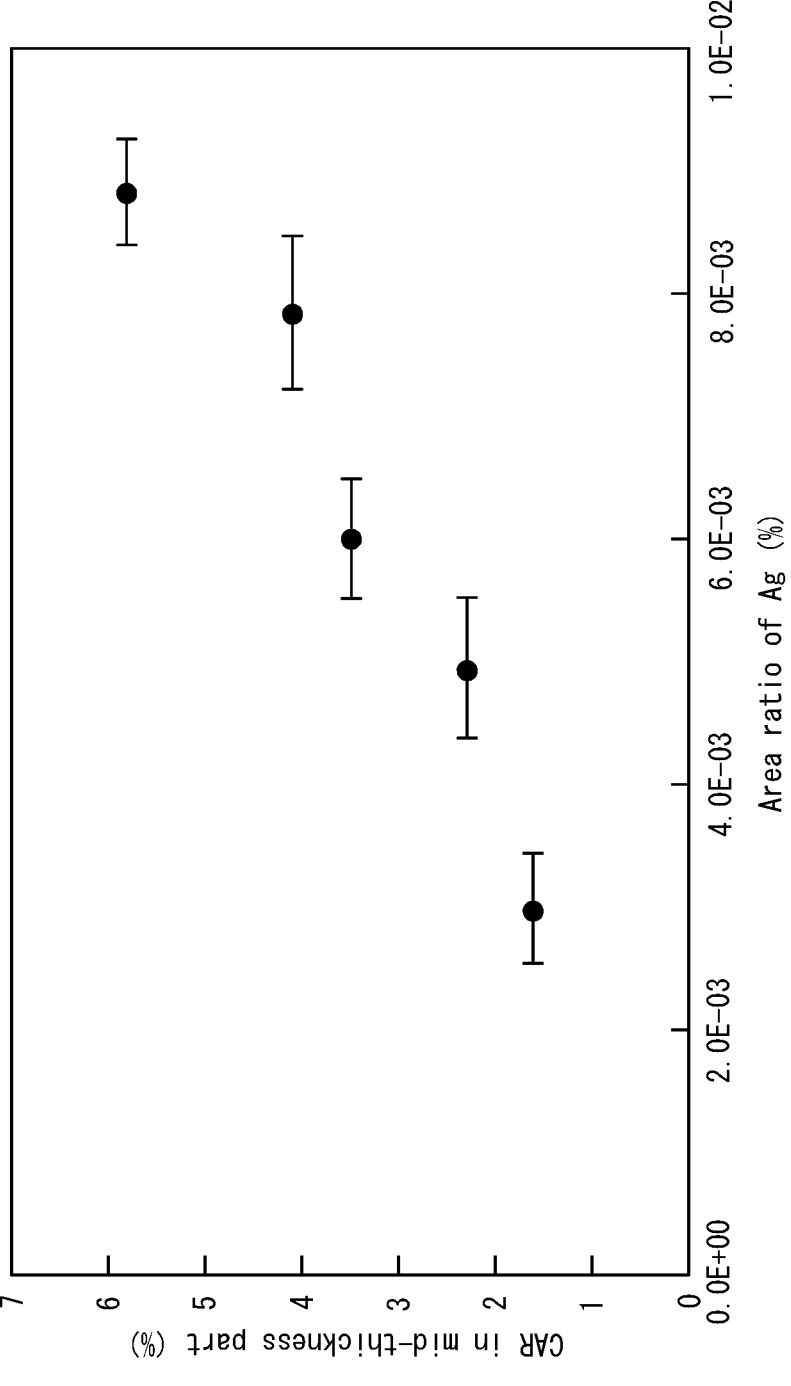

The following provides details of a method of carrying out the present disclosure. The following merely provides preferred embodiments of this disclosure, and this disclosure is by no means limited to the disclosed embodiments.

A method of evaluating central segregation in steel according to one embodiment of the present disclosure comprises the steps of: (1) preparing a sample; and (2) measuring the area ratio of an inclusion. As used herein, an "inclusion" is a compound, such as MnS, that is present in a central segregation area in steel and contains a segregation metal element, and includes both a compound that has been present in molten steel (i.e., a primitive inclusion) and a compound that precipitates in the process of solidification of the molten steel (sometimes referred to as a precipitate). The operations performed in each step will be described below.

(1) Step of Preparing Sample

The object of evaluation in the present disclosure is steel, and the present disclosure is applicable to all of a cast steel, a steel plate, and a steel sheet. From the viewpoint of the industrial usefulness of the information obtained by the evaluation method disclosed herein, the present disclosure is suitably applicable, in particular, to steel plates for line pipes or gas tanks, where HIC resistance is important, and to cast steel for such steel plates.

First, the method disclosed herein comprises taking a sample from a steel to be evaluated, the sample having a cross section including a central segregation area. Since central segregation may be non-uniform in the widthwise direction, the cross section is preferably a C-section (i.e., a cross section perpendicular to the casting direction for cast steel or perpendicular to the rolling direction for steel plates and steel sheets). Since a central segregation area exists in the central part in the thickness direction, the sample is taken from the mid-thickness part. The size of the sample is not particularly limited, yet should be representative and fit into the sample chamber of the elemental analyzer. In evaluation using SEM or EPMA, up to about 100 mm square is preferred. An appropriate region in the cross section including a central segregation area is a "region to be measured," which is subjected to the measurement described below.

Then, the method disclosed herein comprises mirror polishing the cross-section of the sample. The polishing can be done by mechanical polishing, electropolishing, or other appropriate methods depending on the sample. If the formation of the inclusion is to be observed more emphatically, the cross section may be lightly etched with nital or the like after polishing.

Then, the method disclosed herein preferably comprises, letting $M_{x1}A_{y1}$ be the inclusion and $N_{x2}A_{y2}$ be a compound with a smaller solubility product than $M_{x1}A_{y1}$, treating the region to be measured in the sample with a solution containing ions of an element N to replace M located on a surface of the inclusion exposed in the region to be measured with N, where M denotes the segregation metal element contained in the inclusion, N denotes a metal element other than M, A denotes an element that combines with the element M to form the inclusion and combines with the element N to form the compound, x1 and y1 each denote a numerical value representing a composition ratio of the inclusion, and x2 and y2 each denote a numerical value representing the composition ratio of the compound.

In other words, as a metal ion N in the solution, a metal ion that forms a compound $N_{x2}A_{y2}$ with a smaller solubility product than the inclusion $M_{x1}A_{y1}$ when combined with an element A may be selected as appropriate. For example, if M is Mn and A is S, i.e., if a focus is placed on $Mn_{x1}S_{y1}$ as inclusions, the major inclusion composition is MnS, yet there are inclusions having various compositions in the steel with x1=1 to 2 when y1=1. In this case, Ag is preferred as the element N to replace Mn. For example, MnS is replaced by $Ag_2S$ and $Mn_2S$ is replaced by AgS. Thus, x2 and y2, which represent the compound composition ratio, can vary depending on the composition ratio of the inclusion.

In the evaluation method using SEM, as described below, an inclusion is first identified using a reflected electron image. In this case, the larger the difference between the average atomic number of the compound after replacing the metal elements in the original inclusion and the atomic number of the Fe matrix, the more clearly the contrast difference is obtained, which is advantageous for identifying an inclusion. Solutions dissolving Ag (solutions containing Ag ions) are preferred from these perspectives, as well as from the perspectives of ease of handling and high detection sensitivity during elemental mapping as described below.

The solvent of the solution is not restricted as long as it can dissolve the target metal and produce metal ions, and both aqueous and non-aqueous solvents can be used. The concentration of metal ions in the solution is also not limited. However, it is preferably about 0.005 mass % or more. It is preferably about 1.0 mass % or less.

When an aqueous solvent is used, the solvent should be an acid such as nitric acid to keep the metal ions stable in the solution. One form of treatment with the solution is to immerse the region to be measured of the sample in a solution containing ions of an element N. The immersion time may be determined according to the sensitivity and accuracy required for the subsequent evaluation. It was confirmed that substitution of metal elements in the inclusion occurred in an extremely short time, for example, in the case of MnS, Ag was found on the surface of the inclusion even after immersion in a nitric acid solution containing 0.1 mass % Ag for 2 seconds to 3 seconds, followed by immediate removal and washing before elemental analysis. In other words, even after a few seconds of immersion, modification of the inclusion progressed to a certain degree. However, from the viewpoint of highly accurate analysis, the immersion time is preferably 5 seconds or more, and more preferably 10 seconds or more. On the other hand, prolonged immersion may cause reaction products to adhere to the sample surface due to corrosion reactions, making it impossible to evaluate the analysis surface. From this perspective, the immersion time is preferably 3600 seconds or less, and more preferably 600 seconds or less.

Another solution-based treatment method is the electrolytic operation using an electrolytic solution containing ions of an element N in a non-aqueous solvent. In this case, it is preferable to add a chelating agent to stably disperse the element N in the electrolyte. Many chelating agents, including but not limited to acetylacetone (AA), can be suitably used. The concentration of the chelating agent may be set appropriately according to the inclusion and substituted metal elements. In this case, from the viewpoint of highly accurate analysis, the electrolysis time (immersion time in the electrolytic solution) is preferably 10 seconds or more, and more preferably 30 seconds or more, under current density conditions for quantitative analysis of the precipitates performed by an ordinary electrolytic extraction method. On the other hand, prolonged electrolysis, in addition to the effect of extraction and replacement of precipitates, may cause significant effects on the base metal structure, such as selective etching at grain boundaries, which may interfere with observation. From this perspective, the electrolysis time (immersion time in the electrolyte) is preferably 1000 seconds or less, and more preferably 500 seconds or less.

(2) Step of Measuring Area Ratio of Inclusion

The method disclosed herein comprises measuring an area ratio of an inclusion containing a segregation metal element in the region to be measured. The area ratio of an inclusion can be measured by elemental analysis. Any instrument capable of elemental analysis, such as SEM-EDS and EPMA, can be used for the analysis. Below is an example of how area ratio is measured for an inclusion.

First, when the sample is treated with a solution containing ions of an element N in the aforementioned step (1), the area ratio of an inclusion in the region to be measured can be obtained indirectly, for example, by the following two methods.

The first method comprises: (i) performing mapping analysis of the element N in the region to be measured using EPMA; (ii) determining an area ratio of a region where the element N is detected at or above a predetermined concentration in the region to be measured; and (iii) using the area ratio as the area ratio of the element N. There are no restrictions on analytical conditions such as accelerating voltage, magnification, etc., as long as the conditions are such that the area of an inclusion can be determined, and the appropriate conditions may be freely selected. In this method, the region where the element N is detected at or above a predetermined concentration is considered to be the region where the inclusion exists, and the area of the region is calculated. The "predetermined concentration" may be set appropriately so that the matrix and inclusion can be distinguished in the sample. The area ratio of the element N can be calculated by dividing the total area of each "region where the element N is detected at or above a predetermined concentration" thus obtained by the area of the region to be measured, and this area ratio is used as the area ratio of the inclusion and evaluated as a central segregation index.

The second method comprises: (i) acquiring an SEM image (e.g., reflected electron image) of the region to be measured; (ii) selecting a candidate region based on contrast in the SEM image, the candidate region being a candidate for the inclusion; (iii) performing SEM-EDS analysis on the candidate region to identify a region where the element N is detected at or above a predetermined concentration; (iv) determining an area ratio of the region identified in the region to be measured; and (v) using the area ratio as the area ratio of the element N. There are no restrictions on analytical conditions such as accelerating voltage, magnification, etc., as long as the conditions are such that the area of an inclusion can be determined, and the appropriate conditions may be freely selected. Although it is generally desirable to evaluate central segregation over a wide range, the aforementioned first method requires a longer analysis time. For the purpose of a quick evaluation, the area ratio of the inclusion can also be obtained from the contrast in the SEM image, instead of the first method, as follows. First, an SEM image (e.g., reflected electron image) of the region to be measured is acquired. An inclusion is identified from the differences in contrast in the acquired SEM image, and the area of the inclusion in the SEM image is calculated. If foreign matter adhering to the region to be measured is observed in similar contrast to the inclusion, the area of the foreign matter may also be counted as the area of the inclusion. To prevent this, SEM-EDS analysis is performed on candidate regions that are candidates for the inclusion to investigate whether they contain the indicator element N. In this case, as in the first method, candidate regions where the concentration of the indicator element N is at or above a preset threshold are regarded as regions where the inclusion exists. By performing SEM-EDS analysis, the area of only those candidate regions containing the indicator element N, i.e., the area of the inclusion, can be calculated from the candidate regions for the inclusion. The SEM-EDS analysis may be performed on the entirety of each candidate region to identify the regions where the element N is detected at or above a predetermined concentration. Alternatively, the SEM-EDS analysis may be performed on the representative position of each candidate region (e.g., the center of gravity position) and if the concentration of the indicator element N is at or above a preset threshold at one position, the corresponding candidate region is considered to be an inclusion and may be identified as a "region where the element N is detected at or above a predetermined concentration." The area ratio of the element N can be calculated by dividing the total area of each "region where the element N is detected at or above a predetermined concentration" thus obtained by the area of the region to be measured, and this area ratio is used as the area ratio of the inclusion and evaluated as a central segregation index.

As explained above, by modifying the surface of an inclusion exposed in the region to be measured with a metal N and measuring the area ratio of N, the area ratio of the inclusion can be accurately determined, making it possible to perform central segregation evaluation with excellent correlation with HIC sensitivity.

Next, if the sample is not treated with a solution containing ions of the element N in the aforementioned step (1), it is necessary to directly measure the area ratio of the inclusion in the region to be measured. In this case, in the first and second methods described above, "element N" should be read as "all constituent elements of the inclusion (e.g., Mn and S)". That is, the first method comprises: (i) performing mapping analysis of all constituent elements of the inclusion (e.g., Mn and S) in the region to be measured using EPMA; (ii) determining an area ratio of a region in where all constituent elements of the inclusion (e.g., Mn and S) are detected at or above a certain concentration in the region to be measured, and (iii) using the area ratio as the area ratio of the inclusion. The second method comprises: (i) acquiring an SEM image (e.g., reflected electron image) of the region to be measured; (ii) selecting a candidate region based on contrast in the SEM image, the candidate region being a candidate for the inclusion; (iii) performing SEM-EDS analysis on the candidate region to identify a region where all the constituent elements of the inclusion (e.g., Mn and S) are detected at or above a predetermined concentration; (iv) determined an area ratio of the region identified in the region to be measured, and (v) using the area ratio as the area ratio of the inclusion.

More advanced central segregation evaluation can also be performed by setting multiple regions to be measured for each position (in the thickness direction) in the cast steel or steel plate.

Examples

The following specifically describes our examples and comparative examples in which Mn was selected as a segregation metal element and the central segregation in each steel plate (plate thickness: 20 mm) was evaluated.

For both our and comparative examples, steel plates with the chemical compositions listed in Table 1 (with the balance being Fe and inevitable impurities) were prepared, and the relationship between central segregation and HIC was investigated. In order to correlate the results of the evaluation of central segregation with CAR, five types of steel plates were prepared, which were manufactured under different manufacturing conditions from each other and had different degrees of central segregation from each other. The dimensions of each sample for central segregation measurement were 80 mm (sheet transverse direction)×10 mm (rolling direction)×20 mm (thickness), and the dimensions of each sample for HIC test were 20 mm (sheet transverse direction)×100 mm (rolling direction)×20 mm (thickness). The C-section of each sample for central segregation measurement was mirror polished to make the analysis surface. The region to be measured, including a central segregation area, was 80 mm in the widthwise direction×15 mm in the thickness direction (±7.5 mm of mid-thickness) for both our and comparative examples. The crack area ratio (CAR (%)) in the HIC test was used as an index of hydrogen-induced cracking resistance. In both our and comparative examples, the reproducibility (repeatability) was also checked by preparing four samples from the same type of steel plate and conducting central segregation measurements and HIC tests.

TABLE 1

|   |   |   |   |   | (mass %) |
|---|---|---|---|---|---|
| C | Si | Mn | P | S | sol. Al |
| 0.04 | 0.17 | 1.4 | 0.005 | 0.0005 | 0.026 |

Our Examples

Each sample thus obtained was immersed in a 1000 mass ppm Ag standard solution (nitric acid based) for 30 seconds to replace Mn located on the surface of $Mn_{x1}S_{y1}$ exposed in the region to be measured with Ag. The sample was then removed and washed with methanol and dried for SEM observation. Setting the accelerating voltage of the SEM to 20 kV and defining the region observed at 200× magnification as one field of view, a reflected electron image was acquired. From the obtained reflected electron image, regions of different contrasts from the base metal were extracted to select candidate regions that were candidates for inclusions. The regions of different contrasts to be extracted were those with an area of 10 μm 2 or more. SEM-EDS analysis was performed on the extracted candidate regions to identify regions where 2 mass % or more of Ag was detected, and the area of such regions was determined. This measurement was repeated in multiple fields of view, and the total area of those regions where 2 mass % or more of Ag was detected was calculated in the entire region to be measured. The total area obtained was divided by the area of the region to be measured to calculate the area ratio of Ag, which was used as the area ratio of an inclusion $Mn_{x1}S_{y1}$.

Comparative Examples

Elemental mapping was performed on the region to be measured in each sample using EPMA. The analysis by EPMA was performed under the following conditions: accelerating voltage: 25 kV, irradiation current: 5 μA, beam diameter: 100 μm, and integration time: 10 msec to measure the concentration distribution of Mn in the region to be measured. Since the beam diameter of EPMA was 100 μm, the measurement was performed for 800×150 points in order to map the entire region to be measured of 80 mm (widthwise direction)×15 mm (thickness direction).

Since each sample was taken from the mid-thickness part including a central segregation area, the upper and lower edges in the thickness direction had the lowest degree of Mn segregation. Therefore, the average concentration of Mn was determined from the measurements for 800×2 points at the top and 800×2 points at the bottom of each sample in the thickness direction, and the result was used as the average Mn concentration ($C_0$) in the steel. The maximum Mn concentration (Cmax) among 150 points along the thickness direction at the same positions in the widthwise direction was also determined. This was done in the widthwise direction of the region to be measured, and the result of averaging the values of Cmax for 800 points was used as the Mn segregation concentration C. The value of C thus obtained was divided by $C_0$, as expressed by $C/C_0$, to calculate the degree of Mn segregation.

[HIC Test]

HIC test specimens were used to determine the crack area ratio (CAR (%)) by performing HIC tests according to the NACE TM0284-96 standard.

Figure 2:
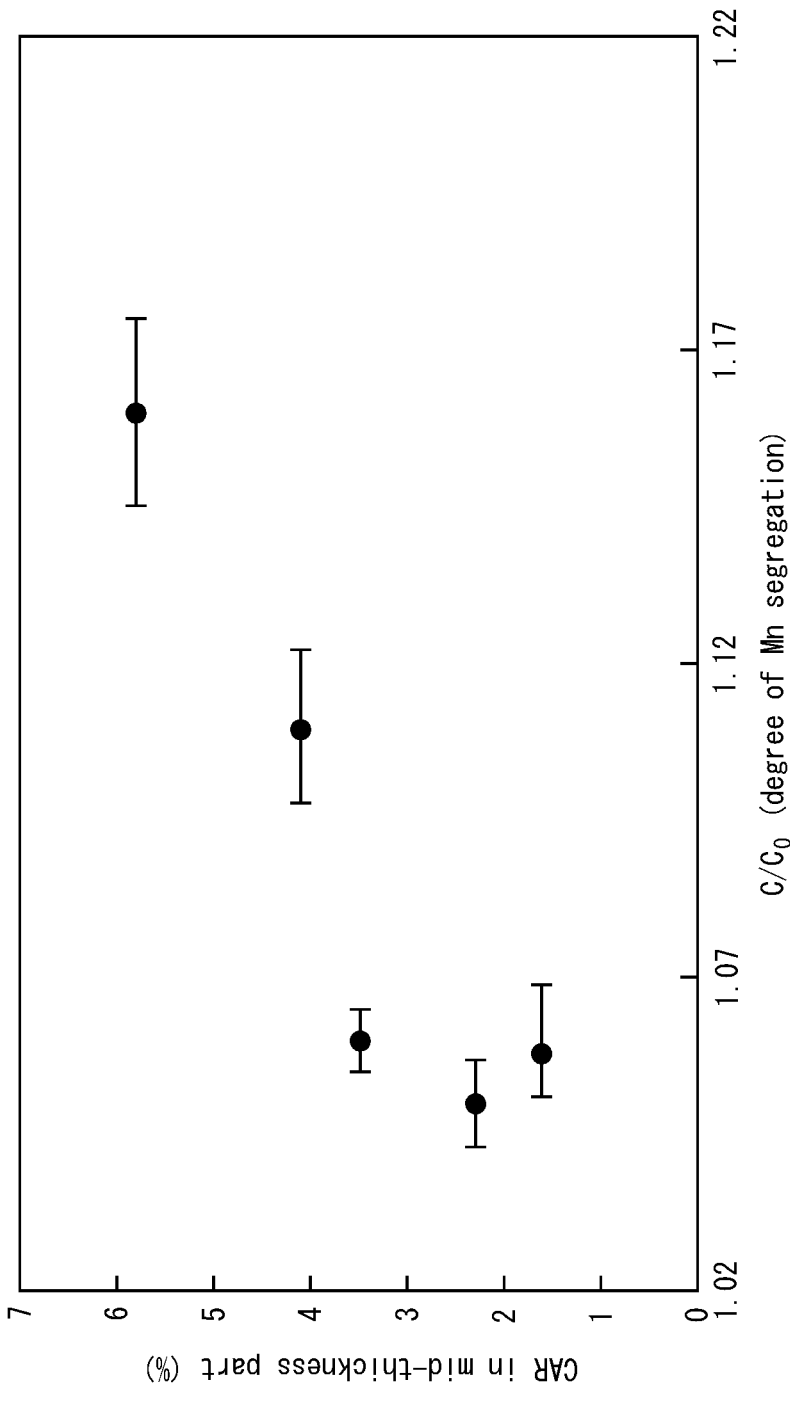
FIG. 2 is a graph of the relationship between the degree of Mn segregation and the CAR in the mid-thickness part in comparative examples.

The relationship between the area ratio of Ag and the CAR in the mid-thickness part in our examples is illustrated in FIG. 1, and the relationship between the degree of Mn segregation and the CAR in the mid-thickness part in the comparative examples is illustrated in FIG. 2. In FIGS. 1 and 2, the error bars are the 26 of the four measurements, and the plots are the average of the four measurements. FIG. 1 demonstrates that the area ratio of Ag was well correlated with CAR in our examples, confirming that the method according to this disclosure is a central segregation evaluation method with excellent correlation with HIC. On the other hand, in the comparative examples illustrated in FIG. 2, no correlation with the degree of Mn segregation was observed in those regions of CAR at or below 3.5%. In FIG. 2, the error bars appear to be small, but this is thought to be due to the fact that the EPMA measurement pitch was 100 μm, which was large for the inclusion, resulting in a small error due to insufficient sensitivity. In other words, even if an inclusion of several μm in size was formed within one measurement region (100 μm), the effect of formation of the inclusion was diluted because the average concentration over the entire region was measured in the comparative examples. Therefore, it cannot be said that the area of an inclusion was precisely determined in the comparative examples, and correlation with CAR is considered difficult to obtain.

From the above, it can be said that the central segregation evaluation method according to the present disclosure enables more precise evaluation of differences in the state of central segregation compared to the conventional methods. The central segregation evaluation method according to the present disclosure can also predict HIC susceptibility, since a good correlation with CAR is obtained.

INDUSTRIAL APPLICABILITY

As described above, the method disclosed herein can accurately evaluate the central segregation state of steel. This makes it possible to determine appropriate manufacturing conditions during casting based on the analyzed central segregation index. As a result, the method disclosed herein is industrially beneficial, for example, in terms of reducing costs by optimizing process conditions.

The invention claimed is:
1. A method of evaluating central segregation in steel, the method comprising:

taking a sample from a steel, the sample having a cross section including a central segregation area;

measuring an area ratio of an inclusion containing a segregation metal element in a region to be measured including the central segregation area in the cross section; and evaluating HIC susceptibility of the steel by evaluating central segregation in the steel based on the area ratio measured, where letting $Mn_{x1}S_{y1}$ be the inclusion and $Ag_{x2}S_{y2}$ be a compound with a smaller solubility product than $Mn_{x1}S_{y1}$, the method further comprising:

treating the region to be measured in the sample with a solution containing Ag ions to replace Mn located on a surface of the inclusion exposed in the region to be measured with Ag;

then, measuring an area ratio of Ag in the region to be measured; and using the area ratio of Ag measured as the area ratio of the inclusion, where x1 and y1 each denote a numerical value representing a composition ratio of the inclusion, and x2 and y2 each denote a numerical value representing a composition ratio of the compound.

2. The method of evaluating central segregation in steel according to claim 1, the method further comprising:

performing mapping analysis of Ag in the region to be measured using EPMA;

determining an area ratio of a region where Ag is detected at or above a predetermined concentration in the region to be measured; and using the area ratio as the area ratio of Ag.

3. The method of evaluating central segregation in steel according to claim 1, the method further comprising:

acquiring an SEM image of the region to be measured;

selecting a candidate region based on contrast in the SEM image, the candidate region being a candidate for the inclusion;

performing SEM-EDS analysis on the candidate region to identify a region where Ag is detected at or above a predetermined concentration;

determining an area ratio of the region in the region to be measured; and using the area ratio as the area ratio of Ag.

4. The method of evaluating central segregation in steel according to claim 3, wherein the SEM image is a reflected electron image.

5. The method of evaluating central segregation in steel according to claim 1, wherein the steel is a cast steel, a steel plate, or a steel sheet.

6. The method of evaluating central segregation in steel according to claim 5, wherein the cross section is a cross section perpendicular to a casting direction of the cast steel, a cross section perpendicular to a rolling direction of the steel plate, or a cross section perpendicular to a rolling direction of the steel sheet.

\* \* \* \* \*